United States Patent [19]

Groen et al.

[11] Patent Number: 4,871,724

[45] Date of Patent: Oct. 3, 1989

[54] NOVEL 11-ARYLOESTRANE AND 11-ARYLPREGNANE DERIVATIVES

[75] Inventors: Marinus B. Groen, Schayk; Hendrik P. de Jongh, Oss, both of Netherlands

[73] Assignee: Akzo N.v., Arnhem, Netherlands

[21] Appl. No.: 183,851

[22] Filed: Apr. 20, 1988

[30] Foreign Application Priority Data

Apr. 24, 1987 [NL] Netherlands ................. 8700970

[51] Int. Cl.$^4$ .............. A61K 31/58; A61K 31/585; A61K 31/56; C07J 1/00
[52] U.S. Cl. ........................ 514/173; 514/175; 514/181; 260/397.3; 260/397.4; 260/397.47; 540/17; 540/23
[58] Field of Search ............ 260/397.3, 397.4, 397.47; 514/172, 173, 175, 181; 540/17, 23

[56] References Cited

U.S. PATENT DOCUMENTS

| | | | |
|---|---|---|---|
| 3,424,769 | 1/1969 | Fried ................. | 260/397.3 |
| 4,386,085 | 5/1983 | Teutsch et al. ........ | 260/397.1 |
| 4,447,424 | 5/1984 | Teutsch et al. ........ | 260/397.1 |
| 4,519,946 | 5/1985 | Teutsch et al. ........ | 260/397.45 |
| 4,536,401 | 8/1985 | Neef et al. ........... | 514/173 |
| 4,609,651 | 9/1986 | Rohde et al. .......... | 514/179 |
| 4,634,695 | 1/1987 | Torelli et al. .......... | 514/178 |

FOREIGN PATENT DOCUMENTS 0193759 8/1986 European Pat. Off. .
2175905 12/1986 United Kingdom .

*Primary Examiner*—Douglas W. Robinson
*Assistant Examiner*—Joseph A. Lipovsky
*Attorney, Agent, or Firm*—William M. Blackstone

[57] ABSTRACT

The present invention is concerned with 11-aryloestrane and 11-arylpregnane derivatives, characterized in that these derivatives have the following structure:

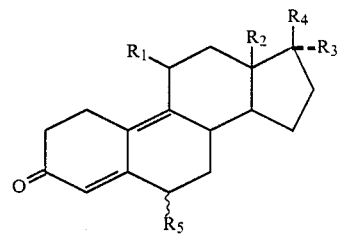

wherein
$R_1$ is an aryl group with an

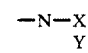

group as substituent,

X and Y each being separately H or a (1-4 C) hydrocarbon radical or together a (2-6 C) hydrocarbon radical;

$R_2$ is an alkyl group containing 1-4 carbon atoms;

$R_3$ is H, OH, a saturated or unsaturated hydrocarbon radical containing 1-8 carbon atoms, at least provided with a hydroxyl, oxo, halogen, azido or nitrile group; an acyloxy or an alkoxy group;

$R_4$ is a hydroxyl, an acyloxy or an alkoxy group or an acyl group optionally provided with a hydroxyl, alkoxy, acyloxy or halogen group; or $R_3$ and $R_4$ together form a ring system; and $R_5$ is a hydrocarbon group containing 1-4 carbon atoms, and further with processes for the preparation of these compounds and with pharmaceutical preparations comprising these compounds. The compounds according to the present invention exhibit antiprogestin activity.

8 Claims, No Drawings

NOVEL 11-ARYLOESTRANE AND 11-ARYLPREGNANE DERIVATIVES

The invention relates to new 11-aryloestrane and 11-arylpregnane derivatives, to methods for the preparation of said compounds, and also to pharmaceutical preparations which contain said derivatives as an active constituent.

Antiprogestins—inter alia—are substances which exhibit affinity for the progesterone receptor, such substances not exerting, or exerting to a considerably reduced extent, the action of progesterone. Antiprogestins are known from the European Patent Application No. 0,057,115.

It has been found, however, that such antiprogestins, in addition to the desired antiprogestin activity, also exhibit an antiglucocorticoid activity which is undesirable if said substances are to be used as antiprogestin agent.

A new group of compounds has now been found which exhibit a strong antiprogestin and a weak or non-existent antiglucocorticoid activity.

The invention therefore relates to said steroids which are characterized in that said steroids have the following formula:

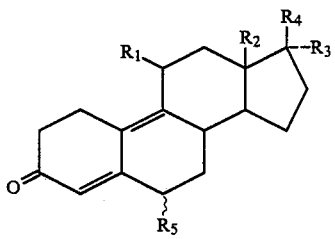

wherein
$R_1$ is an aryl group with an

group as substituent X and Y each being separately H or a (1–4 C) hydrocarbon radical or together a (2–6 C) hydrocarbon radical;

$R_2$ is an alkyl group containing 1–4 carbon atoms;

$R_3$ is H, OH, a saturated or unsaturated hydrocarbon radical containing 1–8 carbon atoms, at least provided with a hydroxyl, oxo, halogen, azido or nitrile group; or an acyloxy or an alkoxy group;

$R_4$ is a hydroxyl, an acyloxy or an alkoxy group or an acyl group optionally provided with a hydroxyl, alkoxy, acyloxy or halogen group; or $R_3$ and $R_4$ together form a ring system; and $R_5$ is a hydrocarbon radical containing 1–4 carbon atoms.

The aryl group in $R_1$ may be derived from, for example, benzene, biphenyl, naphthalene, anthracene or phenantrene. Phenyl is the most preferred. The substituent is situated in the case of a phenyl group preferably in the meta or para position.

The substituent on the aryl group is a group with the formula

The (1–4 C) hydrocarbon radical in X and Y may, inter alia, be methyl, ethyl, vinyl, ethynyl, propyl, 2-propenyl, allenyl, 1-propynyl, butyl and branched analogues thereof. If X and Y together form a (2–6 C) hydrocarbon radical, the hydrocarbon radical may be saturated or unsaturated; preferably, the hydrocarbon radical contains 4 or 5 carbon atoms. Preferably, X and Y are a saturated alkyl group containing 1–3 carbon atoms and, still more preferably, methyl. $R_2$ is preferably ethyl or methyl and, still more preferably, methyl. The (1–8 C) hydrocarbon radical $R_3$ may, inter alia, be 3-hydroxy-1-propynyl, 3-hydroxy-1-propenyl, chloroethynyl, bromoethynyl and 3-hydroxypropyl. The acyloxy group $R_3$ and $R_4$ is preferably derived from an organic carboxylic acid containing 1–18 C atoms such as acetic acid, propionic acid, butyric acid, trimethylacetic acid, phenylacetic acid, cyclopentylpropionic acid, phenylpropionic acid, valeric acid, caproic acid, pelargonic acid, lauric acid, palmitic acid, benzoic acid or succinic acid.

The alkoxy group $R_3$ and $R_4$ is preferably derived from an ether containing 1–12 C atoms such as, for example, methyl ether, ethyl ether, cyclopentyl ether, benzyl ether and tetrahydropyranyl ether.

The acyl group $R_4$, optionally substituted by a hydroxyl, alkoxy, acyloxy or halogen group, is preferably derived from an organic carboxylic acid containing 1–18 C atoms such as those already mentioned above. Examples of suitable substituted acyl groups are hydroxyacetyl, fluoroacetyl, chloroacetyl and propionyloxyacetyl.

If $R_3$ and $R_4$ together denote a ring system, the preference is for heterocyclic ring systems containing 5 atoms in the ring and, in particular, for ring systems in which the ring is bonded to position 17$\beta$ of the steroid skeleton by means of an oxygen atom which forms part of the ring. The greatest preference is for the following heterocyclic ring systems:

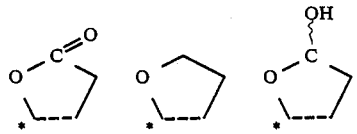

where the carbon atom which is provided with an * is the carbon atom in position 17 of the steroid skeleton.

In the case of $R_3$ and $R_4$ not together denoting a ring system, the greatest preference for $R_3$ is for a saturated or unsaturated alkyl group containing 1–4 carbon atoms substituted at least with a hydroxyl or oxo group, and for $R_4$ for a hydroxyl group.

With still greater preference, $R_3$ is an unsaturated alkyl group containing 1–4 carbon atoms and containing 1 or 2 hydroxyl groups.

$R_5$, which group may be bonded to position 6$\alpha$ or 6$\beta$ of the steroid skeleton, is a hydrocarbon group containing 1–4 carbon atoms, such as methyl, ethyl, propyl, isobutyl, ethenyl, ethinyl, propenyl and butenyl. Preferably, $R_5$ is an alkyl group containing 1–4 carbon atoms. For $R_5$, the greatest preference is for methyl.

The invention also relates to pharmaceutical preparations which contain one or more of the compounds according to the invention as active constituent. The novel compounds can be administered orally, intravaginally or parenterally in the normal manner, in combination with pharmaceutically auxiliary substances, in the form of tablets, pills, dragees and other normal dosage forms. The dosage forms can be prepared according to known galenic procedures.

The administered amount of the compounds according to the present invention may vary within wide ranges, e.g. 50–1000 mg and preferably 100–800 mg during a therapy which may last 1–10 days. If a one-day therapy is applied, the amount administered may vary between e.g. 200 and 1000 mg. If, on the other hand, a longer therapy, e.g. 5 days, is applied the administered amount each day is lower, e.g. 10–200 mg.

The compounds according to the present invention can be prepared by starting from 11β-hydroxyoestr-5-ene-3,17-dione-3,17-diketal or a corresponding 18-(1–3 C)-alkyl compound. The ketal groups have the formula:

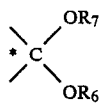

wherein $R_6$ and $R_7$ denote an alkyl group containing 1–4 carbon atoms or $R_6$ and $R_7$ together form an alkylene group containing 2–5 carbon atoms and wherein * indicates the carbon atom at position 3 and 17 of the steroid skeleton. This compound is epoxidized, for example with m-chloroperbenzoic acid in $CH_2Cl_2$ to the corresponding 5α, 6α-epoxy compound. After this compound has been reacted with a Grignard reagent such as $R_5MgCl$, the corresponding 5α,11β-dihydroxy-6β-$R_5$ compound is obtained. After a double dehydration, for example by means of phosphorusoxychloride (yields $\Delta^{5(10)}$, $\Delta^{9(11)}$) deketalization (yields 3,17-diketo) and selective ketalization, a 6β-$R_5$- $\Delta^{5(10)}$, $\Delta^{9(11)}$-oestradiene-3,17-dione-3-ketal is obtained, or a corresponding 18-(1–3 C)alkyl compound. The 3-ketal group has the same formula as shown above. The selective ketalisation is carried out in an $R_6OH$ alcohol in the presence of an acid as catalyst; in this case, $R_7$ is the same as $R_6$. If the reaction is carried out in the presence of a diol, a ketal is obtained in which $R_6$ and $R_7$ together form an alkylene group.

If the above-mentioned 5α,11β-dihydroxy-6β-$R_5$ compound is successively deketalized/dehydrated (yields the corresponding 11β-hydroxy-6α-$R_5$- 4-ene-3,17-dione), dehydrated (yields the corresponding 6α-$R_5$- $\Delta^4$, $\Delta^{9(11)}$-diene-3,17-dione) and selectively ketalized, a 6α-$R_5$- $\Delta^{5(10)}$, $\Delta^{9(11)}$-oestradiene-3,17-dione-3-ketal is obtained, or a corresponding 18-(1–3 C)alkyl compound.

Starting from said compounds and the above-mentioned corresponding 6β-$R_5$ compounds, the groups in positions 11 and 17 in the steroid skeleton can now be introduced.

Thus, after reduction of the 17-keto group to 17β-OH,17α-H with e.g. $NaBH_4$ and after epoxidation of the $\Delta^{5(10)}$ double bond, for example with m-chloroperbenzoic ac in $CH_2Cl_2$ and $NaHCO_3$, the $R_1$ group can be introduced with simultaneous formation of an OH group in position 5α and displacement of the double bond from 9(11) to 9(10) by reaction with an $R_1$-containing compound $R_1$-metal-X, X being a halogen atom, such as $R_1MgBr$, preferably in the presence of CuCl in tetrahydrofuran or with an $R_1Li$ compound. After dehydration and hydrolysis (for example in 80% acetic acid at 75° C. or in 2N HCl in acetone) compounds according to the present invention are obtained with $R_3 = H$ and $R_4 = OH$.

Another method of preparing compounds according to the present invention is to react the selectively ketalized compound with an $R_3$-metal compound (yields 17α-$R_3$, 17β-OH) in order subsequently to be epoxidized and reacted with an $R_1$-containing compound $R_1$-metal-X, wherein X is a halogen atom, such as $R_1MgBr$, preferably in the presence of CuCl in tetrahydrofuran or with an $R_1Li$ compound. Finally, the compound should also be dehydrated and hydrolyzed (yields 3-keto, $\Delta^4$). Said steps are carried out analogously to the corresponding steps already described. The incorporation of $R_1$ and $R_3$ may also be conducted in the reverse order: in that case the selectively ketalized compound is epoxidized, reacted with $R_1MgBr$ in the presence of CuCl, reacted with $R_3MgBr$ or $R_3Li$, dehydrated and hydrolyzed.

A variant of the initial introduction of the groups in position 17 and subsequently in position 11 is the following. First a group, comprising an oxygen atom which has been protected, is introduced at 17α after the selective ketalization of the 6α- or 6β-$R_5$ compound already described, under the conditions already described. This yields a corresponding compound with said group in position 17α and 17β-OH. Subsequently, group $R_1$ is introduced analogously in the manner already described. Subsequently, if desired, unsaturated bonds optionally present in the group introduced at 17α are reduced. Dehydration and hydrolysis are subsequently carried out with simultaneous splitting off the protective group in the 17α substituent so as to form compounds according to the present invention with 17β-OH, 17α-$R_3$. The group to be introduced according to this variant at 17α is preferably an alkyl, alkenyl or alkynyl ether. The greatest preference is for groups with a terminal tetrahydropyranyl group. In the step in which a part of the group introduced at 17α is split off, the ether group and, preferably, the tetrahydropyranyl group is then split off to form an alkyl, alkenyl or alkynyl group with a terminal hydroxy group. Optionally, said group may be cyclized with the 17β-OH group.

Another method of preparing compounds according to the present invention is to etherify or to esterify the 17-OH group after the selective ketalization. After compounds according to the present invention have been obtained in which $R_3$ or $R_4$ is OH, the hydroxyl group may then, if desired, be esterified or etherified according to methods known per se to obtain other compounds according to the invention.

The compounds according to the invention are obtained by dehydrating and hydrolyzing a compound having the formula:

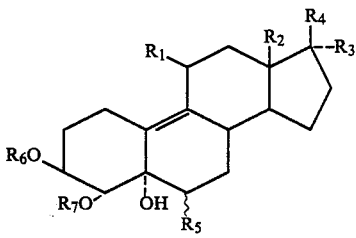

wherein $R_1$, $R_2$, $R_3$, $R_4$ and $R_5$ have the same meaning as has already been described, with the proviso that if $R_3$ and/or $R_4$ denote an oxygen-containing group, $R_3$ and $R_4$ may also be an oxygen-containing group in which the oxygen atom is protected by means of a hydrolyzable group, and wherein $R_6$ and $R_7$ denote an alkyl group containing 1–4 carbon atoms or $R_6$ and $R_7$ together form an alkylene group containing 2–5 carbon atoms, to form compounds according to the present invention. Preferably, the dehydration and the hydrolysis are carried out in one stage. The temperature at which this stage is carried out is in general between 10° and 90° C.; the reaction time is usually 15 minutes to 4 hours. The dehydration/hydrolysis step is carried out according to a method known per se and using agents known per se such as, for example, with acetic acid or with HCl in acetone.

The invention is explained in more detail by means of the following examples.

EXAMPLE 1 a. A solution of 44 g of m-chloroperbenzoic acid (content: 80%) in 0.5 l of methylene dichloride was added dropwise at −20° C. to a solution of 70 g of 11β-hydroxyoestr-5-ene-3,17-dione-3,17-diethyleneacetal in 1,4 l of methylene dichloride. The solution obtained was stirred for 2 hours at −15° C. and then poured out into 1 l of 1N sodium hydroxide. The organic layer was separated off, washed with 500 ml of 5% sodium sulphite solution, 500 ml of 1N sodium hydroxide and 500 ml of water. The solution obtained was dried on anhydrous potassium carbonate, filtered and evaporated down to approx. 100 ml. The residue was stirred for some time with 200 ml of diisopropylether, after which the precipitate obtained was filtered off. Yield: 57 g of 5α, 6α-epoxy-11β-hydroxyoestrane-3,17-dione-3,17-diethyleneacetal.

b. To a solution of the latter in 400 ml of dry toluene, 350 ml of a 1.4M solution of methyl magnesium chloride in tetrahydrofuran were added dropwise. The mixture obtained was boiled for 1 hour with reflux cooling after which it was cooled and poured out into an ice-cold mixture of 200 ml of saturated ammonium chloride solution and 800 ml of water. Extraction was then carried out with ether (3×500 ml). The extract were washed with water, dried on anhydrous sodium sulphate and evaporated down. The residue was recrystallized from diisopropyl ether, 41.3 g of pure 5α,11β-dihydroxy-6β-methyloestrane-3,17-dione-3,17-diethyleneacetal being obtained.

c. 15.0 g of the latter were dissolved in 75 ml of dry dimethyl formamide and 75 ml of dry pyridine. After cooling to 0° C., 15 ml of phosphorus oxychloride were added to this solution at a temperature of <5° C. evaporated down in vacuo. The new product obtained (15.0 g) was purified by chromatography using silica gel. 8.0 g of 6β-methyloestra-5(10),9(11)-diene-3,17-dione-3,17-diethyleneacetal were obtained as a colourless oil. $[\alpha]_D^{20} = +109°$.

d. 15.0 g of this product were dissolved in 150 ml of 70% acetic acid and heated for 1 hour at 50° C. The reaction mixture was poured out into sodium hydrogencarbonate solution and extracted with ether. The ether layers were washed until neutral, dried and evaporated to dryness in vacuo. Yield: 12.0 g of 6β-methyloestra-5(10),9(11)-diene-3,17-dione as a colourless oil. $[\alpha]_D^{20} = +291°$.

e. 12.0 g of this product were dissolved in 170 ml of methanol. After 5.7 g of malonic acid had been added, stirring was carried out for 6 hours at room temperature. The solution was neutralized with sodium hydrogencarbonate solution and extracted with ether. The ether layers were washed until neutral, dried and evaporated down. 12.5 g of a crude product were obtained which was purified by chromatography using silica gel. 9.0 g of 6β-methyloestra-5(10),9(11)-diene-3,17-dione 3,3-dimethylacetal were obtained as a colourless oil. $[\alpha]_D^{20} = +254°$.

f. A solution of 21.0 g of propargyl alcohol tetrahydropyranyl ether in 120 ml of dry THF was added dropwise in 15 min to a solution of ethyl magnesium bromide prepared from 3.0 g of magnesium and 10.2 ml of ethyl bromide in 110 ml of THF. After stirring for 30 min., a solution of 10 g of 6β-methyloestra-5(10), 9(11)-diene- 3,17-dione 3,3-dimethylacetal in 90 ml of THF was added dropwise. After being stirred for 3 hours, the reaction mixture was poured out into 500 ml of a 10% NH₄Cl solution and extracted with ether (3×300 ml). The ether extracts were washed with water, dried on anhydrous Na₂SO₄ and evaporated down. The residue was chromatographed using silica gel, 9.6 g of 17β-hydroxy-6β-methyl-17α-(3-tetrahydropyranyloxy-1-propynyl)oestra-5(10),9(11)-diene-3-one 3,3-dimethylacetal being obtained.

g. 9.3 g of the product obtained in step 1f. were dissolved in 200 ml of methylene chloride. After 5.0 g of sodium hydrogencarbonate had been added, cooling was carried out to −30° C. and 5.4 g of m-chloroperbenzoic acid were added scoop-wise after which stirring was carried out for a further 3 hours between −10° and 0° C. Sodium hydroxide solution was now added and the reaction mixture was extracted with ethyl acetate, the organic layers were washed once with sulphite solution and then washed until neutral, dried and evaporated down in vacuo. 10.1 g of amorphous product were obtained which consisted of a mixture of epoxides which was processed further in the crude state.

h. 1.23 g of copper(I)chloride was added at −10° C. to a solution of p-dimethylaminophenyl magnesium bromide in tetrahydrofuran prepared from 5.23 g of magnesium, 180 ml of tetrahydrofuran and 40 g of p-bromodimethylaniline. After stirring for ¼ hour a solution of 10.1 g of the product obtained in step 1 g. in 120 ml of tetrahydrofuran was added at −10° C. After being stirred for 2.5 hours at room temperature, the solution was poured out into an ammonium chloride solution and extracted with ethyl acetate. The organic layers were washed until neutral, dried, evaporated down in vacuo and the residue was chromatographed using silica gel. 10.1 g of crude product were obtained which were heated with 150 ml of 70% acetic acid for 2.5 hours at 50° C. After neutralization with sodium hydrogencarbonate, extraction was carried out with ether. The organic layers were washed until neutral, dried and evaporated down in vacuo. The residue was purified by chromatography using silica gel. 5.29 g of pure 11β-[4-(dimethylamino)phenyl]-17β-hydroxy-17α-(3-hydroxy-1-propy-nyl)-6β-methyloestra-4,9-diene-3-one were obtained as a yellow amorphous substance; $[\alpha]_D^{20} = +170°$ (c=1, CHCl$_3$).

EXAMPLE 2

3.5 g of 11β-[4-(dimethylamino)phenyl]-17β-hydroxy-17α-(3-hydroxy-1-propynyl)-6β-methyloestra-4,9-diene-3-one were dissolved in 250 ml of absolute ethanol and hydrogenated in the presence of 2.8 g of Lindlar catalyst until 1 equivalent of hydrogen had been absorbed (1.5 hours). The catalyst was filtered off and the filtrate evaporated down in vacuo. After chromatography using silica gel, 2.4 g of 11β-[4-(dimethylamino)-phenyl]-17β-hydroxy-17α-(3-hydroxy-1-(Z)-propenyl)-6β-methyloestra-4,9-diene-3-one were obtained; $[\alpha]_D^{20} = +185°$ (c=1, CHCl$_3$).

EXAMPLE 3

A solution of 2 g of 11β-[4-(dimethylamino)phenyl]-17β-hydroxy-17α-(3-hydroxy-1-propynyl)-6β-methyloestra-4,9-diene-3-one in 200 ml of a 1/1 mixture of toluene and ethanol was hydrogenated in the presence of 200 mg of 5% Pd-BaSO$_4$ until 2 equivalents of hydrogen had been absorbed. The catalyst was filtered off and the filtrate evaporated down. Chromatography using silica gel yielded 1.2 g of amorphous 11β-[4-(dimethylamino)phenyl]-17β -hydroxy-17α-(3-hydroxy-1-propyl)-6β-methyloestra-4,9-diene-3-one; $[\alpha]_D^{20} = +196°$ (c=1, CHCl$_3$).

EXAMPLE 4

A solution of 10 g of 11β-[4-(dimethylamino)phenyl]-17β-hydroxy-17α-(3-hydroxy-1-propyl)-6β-methyloestra-4,9-diene-3-one in 200 ml of methylene dichloride was added to a stirred suspension of 15 g of pyridinium chlorochromate in 200 ml of methylene dichloride. The mixture obtained was stirred for 30 minutes at 20° C., diluted with 400 ml of ether and filtered using hyflo. The filtrate was concentrated and chromatographed using silica gel. In this manner, 4.5 g of 11β-[4-(dimethylamino)phenyl]-17β-hydroxy-6β-methyl-3-oxo-19-nor-17α-pregna-4,9-diene-21-carboxaldehyde were obtained, very predominantly in the form of the cyclic semi-acetal. This product was dissolved in 400 ml of toluene and, after 45 g of silvercarbonate/Celite (Fetizon's reagent) had been added, it was boiled for 5 hours with reflux cooling. 22.5 g of silvercarbonate/Celite was then again added and boiling was carried out for a further 2 hours. The reaction mixture was cooled, filtered and evaporated down. The residue was chromatographed over silica gel, 3.0 of 11β-[4-(dimethylamino)phenyl]-17β-hydroxy-6β-methyl-3-oxo-19-nor-17α-pregna-4,9-diene-21-carboxylic acid gamma-lactone being obtained as a yellow amorphous substance; $[\alpha]_D^{20} = +144°$ (c=1, CHCl$_3$).

EXAMPLE 5

0.6 g of p-toluenesulphonyl chloride was added to a solution of 1.2 g of 11β-[4-(dimethylamino)phenyl]-17β-hydroxy-17β-(3-hydroxy-1-propyl)-6β-methyl-Δ$^{4,9}$-oestra-diene-3-one in 15 ml of pyridine. After stirring for 6 hours, 100 ml of water were added, after which the mixture obtained was extracted with ether. The extracts were washed 5 times with water, dried on anhydrous Na$_2$SO$_4$ and evaporated down. The residue was chromatographed using silica gel with toluene-/ethyl acetate 1/1. This yielded 0.7 g of pure 11β-[4-(dimethylamino)phenyl]-6β-methyl-4',5'-dihydrospiro-[oestra-4,9-diene-17,2' (3'H)-furan]-3-one; $[\alpha]_D^{20} = +197°$ (c=1, CHCl$_3$).

EXAMPLE 6

(a) 150 ml of 4N hydrochloric acid were added to a solution of 39 g of 5α,11β-dihydroxy-6β-methyloestrane-3,17-dione-3,17-diethyleneacetal in 550 ml of acetone. The mixture obtained was boiled for 4 hours under reflux cooling, cooled, evaporated down to a small volume and diluted with water (200 ml). Extraction was then carried out with ethyl acetate (3×200 ml), after which the extracts were washed with water, dried on anhydrous sodium sulphate and eva-porated down. The residue was recrystallized from diiso-propyl ether. The crystals obtained were then recrystal-lized from acetonitrile, 14.2 g of pure 11β-hydroxy-6α-methyloestr-4-ene-3,17-dione being obtained.

(b) 10 ml of thionyl chloride were added dropwise in the course of 30 min. to a solution of 8.85 g of 11β-hydroxy-6α-methyloestr-4-ene-3,17-dione in 150 ml of dry pyridine at −35° C. while stirring thoroughly. After stirring for 45 minutes at −15° C., the reaction mixture was poured out into 1 l of ice-water. Extraction with metylene dichloride yielded an organic layer which was washed with water until neutral, dried on sodium sulphate, filtered and evaporated to dryness in vacuo. Yield: 9 g of 6α-methyloestra-4,9(11)-diene-3,17-dione.

(c) The 9 g of 6α-methyloestra-4,9(11)-diene-3,17-dione thus obtained in crude form were dissolved in 275 ml of methanol and cooled to 0° C. 1.1 ml of acetyl chloride were added to this cooled solution at 0°-5° C. while stirring. After stirring for 30 minutes at 0°-5° C., the reaction mixture was neutralized by adding a saturated sodium bicarbonate solution and then pouring out into 200 ml of water. Extraction with methylene dichloride yielded an organic layer which was washed with water until neutral, dried on sodium sulphate, filtered and evaporated to dryness in vacuo. After purification by chromatography using silica gel, 2.5 g of pure 6α-methyloestra-5(10), 9(11)-diene-3,17-dione 3-dimethylacetal were obtained.

(d) In a manner analogous to that described in Example 1f.-1h., the compound obtained in Example 6c. was converted into 11β-(4-dimethylaminophenyl)-17β-hydroxy-17β-(3-hydroxy-1-propynyl)-6α-methyloestra-4,9-diene-3-one; $[\alpha]_D^{20} = +24°$ (c=1,dioxane). In a manner analogous to that described in Examples 2-5, the following compounds were prepared:

11β-[4-(dimethylamino)phenyl]-17β-hydroxy-17α-(3-hydroxy-1-(Z)-propenyl)-6α-methyloestra-4,9-diene-3-one, 11β-[4-(dimethylamino)phenyl]-17β-hydroxy-17α-(3-hydroxy-1-propyl)-6α-methyloestra-4,9-diene-3-one, 11β-[4-(dimethylamino)phenyl]-17β-hydroxy-6α-methyl-3-oxo-19-nor-17α-pregna-4,9-diene-21-carboxaldehyde, 11β-[4-(dimethylamino)phenyl]-17β-hydroxy-6α-methyl-3-oxo-19-nor-17α-pregna-4,9-diene-21-carboxylic acid gamma-lactone, and 11β-[4-(dimethylamino)phenyl]-6α-methyl-4',5'-dihydrospiro-[oestra-4,9-diene-17,2'(3'H)-furan]-3-one.

EXAMPLE 7

(a) 43.6 g of magnesium turnings were suspended in 150 ml of dry tetrahydrofuran. A solution of 134 ml of ethyl bromide in 350 ml of dry tetrahydrofuran was then added dropwise while stirring well in a nitrogen atmosphere. The mixture was then stirred for 15 minutes at reflux temperature. After cooling to room temperature, a suspension of 44 g of 5α,6α-epoxy-11β-hydroxy-oestrane-3,17-dione-3,17-diethyleneacetal in 500 ml of dry toluene was added. After being stirred for 24 hours at room temperature followed by 30 minutes at reflux temperature, the reaction mixture was cooled to room temperature and carefully poured out into a mixture of 750 ml of saturated ammonium chloride solution and 3 l of ice-water. Extraction with methylene dichloride yielded an organic layer which was washed with water until neutral, dried on sodium sulphate filtered and evaporated down in vacuo. After recrystallization from diethyl ether, 20 g of pure 5α,11β-dihydroxy-6β-ethyl-oestrane-3,17-dione-3,17-diethyleneacetal were obtained. Melting point: 171.2° C.; $[\alpha]_D^{20} = -24°$ (c=1%, dioxane).

After the mother liquor had been purified by chromatography using silica gel followed by crystallization, a further 11.8 g of said pure product were obtained.

(b) To a solution of 20.3 g of this product in 190 ml of dry pyridine and 190 ml of dry dimethyl formamide 40 ml of phosphorusoxychloride were added at 35 minutes at 0° C. while stirring well in a nitrogen atmosphere. The temperature was then raised to 50° C. After being stirred for 6 hours at 50° C., the reaction mixture was cooled to 0° C. and carefully neutralized with 400 ml of 5M potassium hydroxide solution. The mixture was then poured out into 1.5 l of water. Extraction with ethyl acetate yielded an organic layer which was washed with water until neutral, dried on sodium sulphate, filtered and evaporated down in vacuo. After purification by chromatography using silica gel, 10.9 g of 6β-ethyloestra-5(10),9(11)-diene-3,17-dione-3,17-diethyleneacetal were obtained; $[\alpha]_D^{20} = +86°$ (c=1%, dioxane).

(c) A solution of 20.6 g of this product in 230 ml of 70% acetic acid was stirred for 1 hour at 50° C. After being cooled to room temperature, the reaction mixture was carefully poured out while stirring well into a solution of 350 g sodium bicarbonate in 1,500 ml of water. The precipitate was filtered off, washed with water until neutral and then taken up in methylene dichloride. This organic solution was dried on sodium sulphate, filtered and evaporated to dryness in vacuo. Yield: 16.1 g of 6β-ethyloestra-5(10),9(11)-diene-3,17-dione.

(d) In the manner described in Example 6c., 13.3 g of 6β-ethyloestra-5(10),9(11)-diene-3,17-dione-3-dimethylacetal, $[\alpha]_D^{20} = +209°$ (c=1%, dioxane), were obtained a acetalization from 16.1 g of 6β-ethyloestra-5(10),9(11)-diene-3,17-dione.

(e) In the manner described in Example 1f–1h and 2–5 this compound was converted into the corresponding 6β-ethyl end-products mentioned in Examples 1h, 2, 3, 4 and 5.

We claim:
1. 11-aryloestrane and 11-arylpregnane derivatives having the following structure:

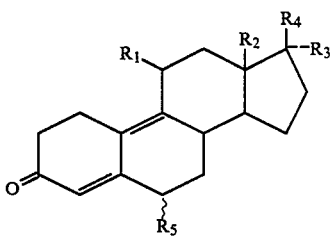

wherein $R_1$ is an aryl group with an

group as substituent, X and Y each being separately or a (1–4C) hydrocarbon radical or together a (2–6 C) hydrocarbon radical;

$R_2$ is an alkyl group containing 1–4 carbon atoms;

$R_3$ is H, OH, a saturated or unsaturated hydrocarbon radical containing 1–8 carbon atoms, at least provided with a hydroxyl, oxo, halogen, azido or nitrile group; and acyloxy or an alkoxy group;

$R_4$ is a hydroxyl, an acyloxy or an alkoxy group or an acyl group optionally provided with a hydroxyl, alkoxy, acyloxy or halogen group; or $R_3$ and $R_4$ together form an oxygen containing heterocyclic 5-member ring system; and $R_5$ is a hydrocarbon group containing 1–4 carbon atoms.

2. Compounds according to claim 1, wherein $R_1$ is an aminophenyl group having the structure

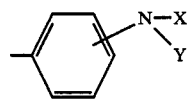

wherein X and Y each separately denote an alkyl group containing 1–4 carbon atoms.

3. Compounds according to claim 1, wherein $R_2$ is methyl.

4. Compounds according to claim 1, wherein $R_3$ is an unsaturated alkyl group containing 1–4 carbon atoms and containing 1 or 2 hydroxyl groups.

5. Compounds according to claim 1, wherein $R_3$ and $R_4$ together form a ring system.

6. Compounds according to claim 1, wherein $R_4$ is a hydroxyl group.

7. Compounds according to claim 1, wherein $R_5$ is an alkyl group containing 1–4 carbon atoms.

8. Pharmaceutical composition comprising at least one of the compounds according to claim 1 in a pharmaceutically effective amount.

* * * * *